United States Patent [19]

Urry

[11] Patent Number: 4,589,882
[45] Date of Patent: May 20, 1986

[54] ENZYMATICALLY CROSSLINKED BIOELASTOMERS

[76] Inventor: Dan W. Urry, c/o Lab. of Molecular Biophysics University of Alabama in Birmingham University Station, P.O. Box 311, Birmingham, Ala. 35294

[21] Appl. No.: 533,524

[22] Filed: Sep. 19, 1983

[51] Int. Cl.⁴ .......................... A61F 2/02; A61F 2/06; A61K 37/00
[52] U.S. Cl. .......................................... 623/11; 623/1; 623/66; 128/334 R; 128/1 R; 424/36; 514/12; 514/17; 530/330; 530/345; 530/409
[58] Field of Search ................... 128/334 R, 1 R; 3/1, 3/1.4, 1.9; 424/36, 177; 260/112.5 R; 528/328, 310; 623/1, 16, 11, 66 B

[56] References Cited

U.S. PATENT DOCUMENTS 4,132,746  1/1979  Urry et al. .......................... 528/328
4,187,852  2/1980  Urry et al. .......................... 3/1.9
4,500,700  2/1985  Urry .................................. 604/8

Primary Examiner—Richard J. Apley
Assistant Examiner—Gregory Beaucage
Attorney, Agent, or Firm—Oblon, Fisher, Spivak, McClelland & Maier

[57] ABSTRACT

A method of repairing a natural elastic system in a human or animal body, which comprises replacing a damaged portion of the system with a shaped artificial elastomeric copolymer comprising an elastomeric component selected from the group consisting of tetrapeptide and pentapeptide repeating units or mixtures thereof wherein the repeating units comprise amino acid residues selected from the group consisting of hydrophobic amino acid and glycine residues and the repeating units exist in a conformation having a $\beta$-turn and a crosslinking component selected from the group consisting of amino acid and peptide residues of the formula

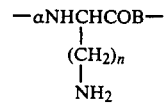

wherein $\alpha$ represents a covalent bond or a peptide fragment containing 1–10 $\alpha$-helix-forming amino acid residues, B represents a covalent bond or a petide fragment containing 1–10 amino acid residues, and n is an integer from 2 to 6; wherein the copolymer optionally comprises a chemotactic component selected from the group consisting of -Ala-Pro-Gly-Val-Gly-Val-, -Pro-Gly-Val-Gly-Val-Ala-, -Gly-Val-Gly-Val-Ala-Pro-, -Val-Gly-Val-Ala-Pro-Gly-, -Gly-Val-Ala-Pro-Gly-Val-, and -Val-Ala-Pro-Gly-Val-Gly- and is essentially devoid of peptide fragments which occur in natural elastin other than these elastomeric, crosslinking, and chemotactic components, is disclosed along with elastomeric copolymers suitable for use in the method of the invention and methods of synthesizing such bioelastomers.

30 Claims, No Drawings

ENZYMATICALLY CROSSLINKED BIOELASTOMERS

BACKGROUND OF THE INVENTION

This work was supported in part by the National Institutes of Health under grant No. HL-29578.

FIELD OF THE INVENTION

This invention relates to bioelastomers, particularly to bioelastomers which can be used as replacements for elastin, and to methods of crosslinking these bioelastomers.

DESCRIPTION OF THE PRIOR ART

Tissue resulting from wound repair, commonly known as scar tissue, is visibly distinct from normal tissue and is generally conceded to be deficient in the elastic fiber component normally present in skin, blood vessels, and related tissue. Previous investigations into the structure of elastic fibers present in blood vessel walls and other elastic materials, such as ligaments, present in humans and animals, has given some insight into the structure of these elastic fibers. The connective tissue of vascular walls is formed from two principal types of protein. Collagen, the principal proteinaceous component of connective tissue, forms the strength-giving structure. In the vascular wall, and particularly in its internal elastic lamina, collagen is associated with natural elastic fibers formed from a different protein, known as elastin. In the relaxed vascular wall, the collagen fibers tend to be folded or crimped, and the elastic fibers are in their retracted state. On distension or stretching, the elastic fibers stretch out, and, as their extension limit is approached, the collagen fibers come into tension to bear the load. As the load diminishes, the elastic fibers draw the wall back to its original dimensions and the collagen fibers back into their folded state. In a synthetic vascular material of the types currently available, such as Dacron, the weave can be viewed as providing the structural analogue of folded collagen, but there is no true elastomeric component.

The central portion of the elastic fibers of vascular wall, skin, lung and ligament is derived from a single protein called tropoelastin. Polypeptide sequences of tropoelastin from vascular wall have been shown by Sandberg and colleagues to contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$, where Ala, Pro, Val and Gly respectively represent alanine, proline, valine and glycine amino acid residues. (Peptide representations in this application conform to the standard practice of writing the NH$_2$-terminal amino acid residue at the left of the formula and the CO$_2$H-terminal amino acid residue at the right). Likewise, the amino acid sequence in the vicinity of natural crosslinks of tropoelastin is known, as disclosed in Gray et al, *Nature*, 246, 461–466 (1973). A high polymer of the hexapeptide has been synthesized, whereby it forms cellophane-like sheets. The hexapeptide was therefore thought to fill a structural role in the natural material. Synthetic high polymers of the pentapeptide and of the tetrapeptide, on the other hand, are elastomeric when cross-linked and appear to contribute to the functional role of the elastic fiber. For example, the chemically cross-linked polypentapeptide can, depending on its water content and degree of crosslinking, exhibit the same elastic modulus as native aortic elastin.

A synthetic polypentapeptide based on the pentapeptide sequence discussed above was disclosed and claimed in U.S. Pat. No. 4,187,852 to Urry and Okamoto. However, the polypentapeptide was crosslinked by modifying one peptide chain to contain free amino groups which reacted with free carboxyl groups present in an adjacent peptide chain. Although this produced a usable material, the insoluble crosslinked polypeptapeptide was totally synthesized under laboratory conditions and was not designed for forming covalent linkages to new tissue being formed in vivo when the crosslinked polypentapeptide was used in an artificial vascular wall substitute. In order to provide the polypentapeptide and related materials in most useful form, it is desirable that they be so constructed as to become covalently crosslinked by tissue enzymes to newly synthesized connective tissue protein. Prior to the present invention, no synthetic elastomeric polypeptide biomaterial was available having the desirable feature of incorporating directly into newly synthesized tissue and no proposal had been made to create any specific material suitable for repairing a natural elastic system of an animal body by incorporating directly into and crosslinking with newly synthesized tissue.

SUMMARY

Accordingly, it is an object of the present invention to provide an elastomeric copolymer functionalized so as to provide reactive groups which can become covalently crosslinked by tissue enzymes to newly synthesized connective tissue protein.

It is also an object of this invention to provide a method of repairing a natural elastic system in a human or animal body with a synthetic elastic material which can be incorporated into the regenerating tissue.

It is a further object of this invention to provide artificial skin, blood vessels, and other artificial replacements for natural elastic systems which can be utilized as prosthetic systems which become incorporated into regenerating tissue.

These and other objects of the invention as will hereinafter become more readily apparent have been accomplished by providing a method of repairing a natural elastic system in a human or animal body, which comprises:

replacing a damaged portion of said system with a shaped artificial elastomeric copolymer, which comprises an elastomeric component selected from the group of tetrapeptide and pentapeptide repeating units or mixtures thereof wherein said repeating units comprise amino acid residues selected from the group consisting of hydrophobic amino acid and glycine residues and wherein said repeating units exist in a conformation having a β-turn and a crosslinking component selected from the group consisting of amino acid and peptide residues of the formula

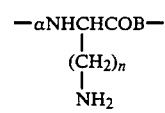

wherein α represents a covalent bond or a peptide fragment containing 1–10 α-helix-forming amino acid residues, B represents a covalent bond or a peptide fragment containing 1–10 amino acid residues, and N is an integer from 2 to 6, wherein said copolymer optionally comprises a chemotactic component selected from the group consisting of Ala-Pro-Gly-Val-Gly-Val, Pro-Gly-Val-Gly-Val-Ala, Gly-Val-Gly-Val-Ala-Pro, Val-Gly-Val-Ala-Pro-Gly, Gly-Val-Ala-Pro-Gly-Val, and Val-Ala-Pro-Gly-Val-Gly and is devoid of peptide fragments which occur in natural elastin other than said elastomeric, crosslinking, and chemotactic components.

This invention also provides elastomeric copolymers suitable for use in preparing shaped artificial bioelastomers.

DESCRIPTION OF THE PREFERRED EMBODIMENTS

The preliminary investigations leading to the present invention were described in prior patent applications by the same inventor, Ser. No. 308,091, filed Oct. 2, 1981, now U.S. Pat. No. 4,474,851 and Ser. No. 452,801, filed Dec. 23, 1982, now U.S. Pat. No. 4,500,700 which are herein incorporated by reference. These applications describe elastomeric peptides which can be utilized to form the elastomeric component of the present invention. An essential feature of the elastomeric polypentapeptide (PPP) and polytetrapeptide (PTP) and of the D-amino-acid-containing pentapeptide of the earlier inventions is the existence of a sequence of regularly appearing $\beta$-turns in the protein's secondary structure, i.e., the conformation of its peptide chain. A $\beta$-turn is characterized by a ten atom hydrogen bonded ring of the following formula:

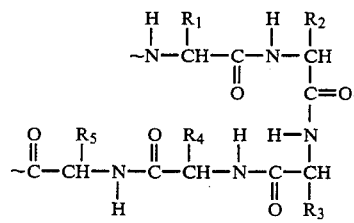

In this formula, $R_1$–$R_5$ represent the side groups of the respective amino acid residues.

The spiral structures produced by a series of $\beta$-turns are more open than the more common $\alpha$-helix. As a result, the atoms between the atoms that participate in hydrogen bonding have a relatively great freedom of movement, more so than in an $\alpha$-helix. This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in hydrogen bonding to other parts of the molecule or to other peptide molecules. Otherwise a greater energy barrier to the libration exists and motion will be restricted. Since non-hydrogen-bonded segments having freedom of motion exist in the $\beta$-spiral between the points of hydrogen bonding for the $\beta$-turns, these segments may be said to be librationally suspended. Librationally suspended segments therefore are a structural feature that exists in the PPP because of the repeating $\beta$-turns with relatively infrequent hydrogen bonding. Librationally suspended segments resulting from the $\beta$-spiral structure and other features still to be discussed are important features that are thought to give rise to elasticity, as will be further discussed.

Another factor leading to the high librational freedom of such molecules is the absence of polar interactions between the amino acid residues, either intrachain or interchain, other than the previously mentioned hydrogen bond. The amino acid residues present are generally all hydrophobic or glycine and accordingly do not exert significant forces on one another through space. If charged or polar groups were present, electrostatic interactions would limit librational freedom and restrict the number of available states in the relaxed (non-extended) form of the molecules. Polar and charged amino acid residues are not strictly prohibited, however, if their presence does not destroy the elasticity of the polypeptide molecule as a whole. For example, an occasional serine residue is present in the polypentapeptide sequence of naturally occurring porcine tropoelastin without destroying elasticity. Accordingly, hydrophobic amino acid residues and glycine are preferred in forming elastomeric polypeptides of the present type although other amino acids may be present to a small extent.

The size of the repeating unit of the elastomeric component is important in determining the stability and dynamic properties of the $\beta$-spiral. Repeating units having fewer than four or more than five amino acid residues do not easily form $\beta$-spirals having the required librational motions. Three amino acid residues are too few for an efficient $\beta$-turn and six residues can result in intervening segments so long that other conformations become energetically more stable. Thus, elastomers of the present type appear to be limited to polypeptides having tetrapeptide or pentapeptide repeating units in the elastomeric component. Elastomers containing an amino acid residue of opposite chirality at position three, as disclosed in the second cited application, are also believed to be limited to polypentapeptides or polytetrapeptides, with polypentapeptides being particularly important.

Selective replacement of glycine residues in the repeating units with hydrophobic D-residues gives an elastomer having a higher modulus of elasticity. Studies of the dominant conformational feature of the polypentapeptide of elastin, the Type II $Pro_2$-$Gly_3$ $\beta$-turn previously discussed, indicate that a D-residue at position three will stabilize the $\beta$-turn. It has now been discovered that substituting a D-amino acid residue for the $Gly_3$ residue produces an elastomeric molecule (after cross-linking) having an elastic (Young's) modulus approximately twice that obtained for the corresponding molecule having a $Gly_3$ residue.

It is preferred that the amino acid residue in position three be a hydrophobic D-amino acid although other D-amino acids are also contemplated to be within the scope of the present invention. Amino acid residues having no more than 10 carbon atoms in their amino acid side chain are preferred. Preferred hydrophobic side chains are alkyl, aryl, and arylalkl, where aryl represents a phenyl or alkyl-substituted phenyl group. Particularly preferred are the residues of D-alanine, D-valine, D-leucine, D-isoleucine, D-phenylalanine, D-2-aminobutanoic acid, and other molecules of similar size, polarity, and chirality. Especially preferred are alkyl side chains having 1–4 carbon atoms in an α-amino acid residue having an α-hydrogen.

The choice of individual amino acids from which to synthesize the remaining sections of the repeating units and resulting polypeptide is unrestricted so long as the resulting structure comprises librationally suspended segments in a β-spiral. The amino acids are not restricted to α-amino acids, although these are preferred, since it has recently become possible to predict the occurrence of β-turns from the α-amino acid sequence of a polypeptide. A review article discussing the prediction of protein conformation, including the prediction of β-turns, was published by Chou and Fasman, *Ann. Rev. Biochem.*, 47, 251 (1978), which is herein incorporated by reference. The size of the side chains present in the hydrophobic amino acids does not greatly affect the β-spiral since the side chains generally extend outward from the surface of the spiral with some important but non-restrictive interturn hydrophobic interactions. However, in order to minimize interchain interactions, it is preferred that the side chain contain no more than 10 carbon atoms. Preferred hydrophobic side chains are the same as those previously described for position three. In addition, it appears from the studies leading to the present invention that preferred side chains of the amino acids are hydrogen or hydrocarbon chains having 1–4 carbon atoms. Examples of especially preferred residues are glycine and the naturally occuring L-amino acids alanine, valine, leucine, and isoleucine as well as closely related molecules such as 2-methyl-2-aminopropanoic acid, L-2-aminobutanoic acid, and L-2-methyl-2-aminobutanoic acid, although it is preferred that the α-carbon have an α-hydrogen. Proline is also a preferred amino acid.

Given positions of the repeating units of the elastomeric component have amino acid residues that are particularly preferred. The first amino acid residue is preferred to be valine, leucine, or isoleucine; the second is preferred to be proline; the third has been previously discussed; the fourth is preferred to be valine, leucine or isoleucine; and the fifth residue is preferred to be glycine. A particularly preferred repeating unit is L-Val-L-Pro-D-Ala-L-Val-Gly.

An elastomeric component consisting entirely of repeating units in which the third amino acid residue is of opposite chirality, as described herein, has an elastic modulus approximately twice that of an otherwise identical polypeptide in which all the amino acids have the same chirality, such as those described in U.S. Pat No. 4,187,852. Accordingly, it is possible to easily alter the elastic modulus by using a mixture of monomers and controlling the amount of crosslinking between adjacent peptide chains. Elastic modulus is proportional to the number of crosslinks, although not in a strictly linear fashion.

A major limitation of the previously discussed polytetrapeptides and polypentapeptides having glycine units at position three is that relatively large cracks, which are visible under the scanning electron microscope, occured during drying of these materials. On the other hand, the D3 analogues are most commonly characterized by the absence of cracking and, when cracking does occur, only smaller cracks appear and then only in limited regions. This suggests that D3 analogues possess greater strength and cohesiveness in the coacervated state, properties which enhance the usefulness of these materials in prosthetic devices.

Because of the chirality of amino acids and of polypeptides produced therefrom, an equally effective polypeptide can be produced by using polypentapeptide repeating units in which all of the amino acids having chiral centers are of the opposite chirality from that previously described; i.e., L-amino acid residues are replaced with D-amino acids. Since both L- and D-amino acids are available commercially and can be used as starting materials in a synthesis of the polypeptide of the invention, for example in the method disclosed later, either of these species of the invention may be easily produced. However, since D-amino acids are relatively more expensive, the more preferred species is that in which all or most of the amino acid residues of the elastomeric component are derived from L-amino acids and only the residue at position 3 is derived from a D-amino acid. Accordingly, the remainder of this disclosure will discuss only predominantly L-amino acid-containing polypeptides since those skilled in the art will recognize that predominantly D-amino acid-containing species can be easily produced in a like manner by a proper selection of amino acid starting materials.

It should be noted that not every amino acid residue in the elastomeric component may be replaced by an amino acid of the opposite chirality. Random replacement leads to destruction of the β-turn and loss of elastic modulus. For example, replacement of an α-hydrogen of the Gly$_5$ residue by a methyl moiety, i.e., synthesis of the L.Ala$_5$ PPP, was carried out as a specific test of the proposed librational freedom mechanism of elasticity. The elastomeric properties in the resulting material were entirely lost even though the β-turn, while weakened, was still present. Likewise, synthesis of a D.Ala$_5$ analog resulted in a material which did not resist the stress of drying. Scanning electron micrographs of a D.Ala$_5$ PPP-Dacron fiber composite showed that the elastomeric matrix ruptures during the stresses of drying and of stretching while wet. Thus, the effect of adding a methyl moiety to the Gly$_5$ residue of the polypentapeptide is to decrease markedly the mobility of the polypeptide chain and to destroy elasticity. Based on structural studies of the β-turn model, it presently appears that only pentapeptides or tetrapeptides in the elastomic component of the invention having the third residue of opposite chirality will retain sufficient librational mobility in a β-turn to produce elasticity according to the mechanism proposed herein.

Methods of preparing elastomeric components in which the third position is occupied by a glycine residue have been disclosed in Rapaka and Urry, Int. J. Peptide Protein Res., 11, 97 (1978), Urry et al, Biochemistry, 13, 609 (1974), and Urry et al, J. Mol. Biol., 96, 101 (1975), which are herein incorporated by reference. The synthesis of these peptides is straightforward and can be easily modified to allow production of a polymer having a D$_3$ residue, if desired. The following summary, which is not to be considered limiting, is an example of one general method of synthesizing the polypeptides.

The first step in the formation of the elastomeric copolymer of the invention usually is synthesis of the various peptide monomers. Any of the classical methods of producing peptide molecules may be used in synthesizing the building blocks of the polymers of the present invention. For example, synthesis can be carried out by classical solution techniques starting from the C-terminal amino acid as a benzyl ester p-tosylate. Each successive amino acid is then coupled to the growing peptide chain by means of a water-soluble carbodiimide and 1-hydroxybenzotriazole. A typically used carbodiimide is 1-(3-dimethylaminylpropyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The first product obtained in the synthesis of the pentapeptide monomer is a protected pentapeptide, such as, Boc-L.Val-L.Pro-D.Ala-L.Val-Gly-OBzl (one of the possible elastomeric components). This protected monomer is converted into the reactive monomer by, for example, replacement of the benzyl ester with the p-nitrophenyl ester, for example by effectively exchanging with p-nitrophenyl trifluoroacetate, and removal of the Boc protecting group. The resulting reactive monomer is polymerized, in the presence any other monomers (such as the other components which are described later) and in the presence of a base such as triethylamine as necessary, to give a polypeptide. A blocking group, such as H-Val-OMe may be added at the conclusion of the polymerization reaction to convert the remaining reactive p-nitrophenyl esters to non-reactive terminal groups if desired.

The structure, synthesis, and use of these elastomeric compounds and of various compositions containing these compounds is fully disclosed in the incorporated patent applications. The present application is not related to these elastomeric components themselves but to elastomeric copolymers comprising elastomeric components of the types described in the above-cited patent applications and in U.S. Pat. No. 4,187,852 and a crosslinking component selected from the group consisting of amino acid and peptide residues of the formula

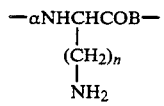

wherein α represents a covalent bond or a peptide fragment containing 1–10 α-helix forming amino acid residues, B represents a covalent bond or a peptide fragment containing 1–10 amino acid residues, and n is an integer from 2 to 6.

The elastomeric copolymers comprising these two components have the same elastomeric properties as previously described and are useful for the same purposes. However, these copolymers have the additional property of being effective substrates for the enzyme lysyl oxidase, a naturally occurring enzyme in tissue which is capable of crosslinking the artificial materials described herein with newly synthesized elastin resulting from the elastin-elaborating fibroblasts present in tissue.

Although it was known that the tropoelastin molecule, the precursor protein of elastin, becomes an irreversibly insoluble fibrous matrix by means of crosslinks derived solely from the 38 lysine residues present in that molecule, not all lysine-containing peptides are capable of acting as substrates for the enzyme lysyl oxidase.

The crosslinking component of present invention resembles the amino acid sequence determined to be present in the crosslinking region of tropoelastin. However, mere knowledge of this sequence was not sufficient to disclose the present invention since, for example, not all peptide sequences are capable of interacting with lysyl oxidase in vivo and becoming incorporated into a regenerating elastic tissue.

Several types of crosslinks result from the action of lysyl oxidase on the crosslinking components. As will be pointed out later, if a set of two lysine residues or the residues of other amino acids having a side chain with a terminal amino group and a 2–6 carbon straight aliphatic chain linking the amino group to the main peptide chain are present in adjacent peptide chains, a desmosine- or isodesmosine-like structure will be produced. If only a single such residue is present in one of the crosslinking components or if two or more residues are present but at the wrong spacing, a linking group of the following formula is formed:

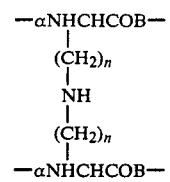

In this formula each α, B, and n have the meanings previously described.

Because of the great stability resulting from enzymatic crosslinking which produces a desmosine- or isodesmosine-like structure, crosslinking components which produce such structures are particularly preferred. By desmosine- and isodesmosine-like structures are meant products of the following formulas:

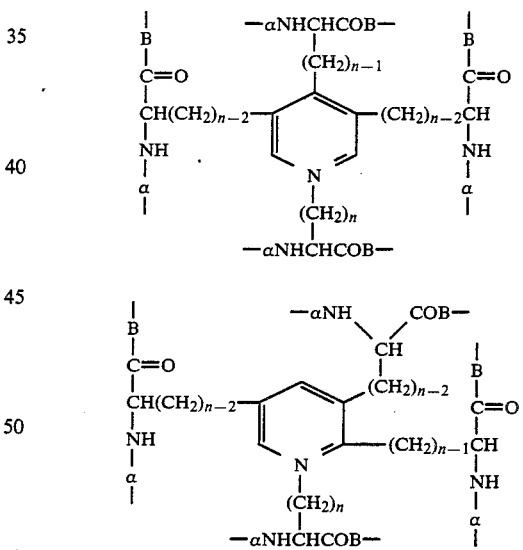

where each n represents an integer from 2 to 6.

In order to encourage the formation of desmosine- and isodesmosine-like structures, various crosslinking components are preferred. Since crosslinking generally occurs in a tropoelastin molecule in an alanine rich section of the peptide chain, α-helix forming amino acid residues are preferably present in the crosslinking component. Various naturally occurring amino acids have different tendencies to form α-helicies. For example, the previously incorporated article by Chou and Fasman classifies protein residues according to their tendency to form α-helix structures as well as other structures. Glutamic acid, alanine, and leucine are strong α-helix formers. Histidine, methionine, glutamine, tryptphan, valine, and phenylalanine are classified as α-helix formers, and lysine and isoleucine are classified as weak α-helix formers. Since, for reasons described in the previous section dealing with the elastomeric component, hydrophobic residues are generally preferred, alanine, leucine, methionine, glutamine, tryptophan, valine, phenylalanine, and isoleucine are preferred α-helix-forming amino acid residues. Of these, alanine and leucine are particularly preferred because of their strong α-helix forming tendencies while alanine is most preferred because of its occurrence in the naturally occurring crosslinking regions of tropoelastin and because of its non-sterically demanding side chain.

Crosslinking components having the formula

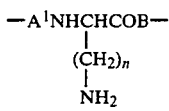

wherein $A^1$ represents a peptide fragment consisting of 2–10 α-helix forming amino acid residues and B has the meaning stated above are preferred crosslinking components. Of these, crosslinking units in which B is $A^2B^1$ wherein $A^2$ represents a peptide fragment consisting of 2 or 3 α-helix forming amino acid residues and $B^1$ represents

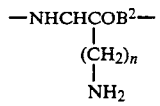

wherein $B^2$ represents a covalent bond or a peptide fragment consisting of 1–6 amino acid residues. In other words, one preferred crosslinking component has two residues with free amino groups separated by two or three α-helix forming amino acid residues with the first free-amine-containing amino acid residue also being preceded in sequence by 2–10 α-helix forming amino acid residues. This provides the proper spacing and α-helical conformation for formation of a desmosine-like structure.

Of crosslinking components having the last formula stated above, those wherein $B^2$ represents 2–4 amino acid residues are preferred. Of these, -Tyr-Gly-Ala- or -Ala-Ala- are preferred.

In all cases, the preferred free-amine-containing amino acid residue is lysine, in which n is 4.

The most preferred crosslinking components are Ala-Ala-Ala-Ala-Lys-Ala-Ala-Lys-Tyr-Gly-Ala and Ala-Ala-Lys-Ala-Ala-Ala-Lys-Ala-Ala.

The various crosslinking components can be synthesized by the same methods previously described for synthesizing other peptide monomers. The only significant difference is the requirement that the Ω-terminal amino group be protected during the synthesis. For example, a benzyloxycarbonyl protecting group may be used as described in U.S. Pat. No. 4,187,852. The resulting crosslinking component monomer is then activated and incorporated into the elastomeric copolymer as described above.

Synthesis of polypeptides containing the elastomer component and crosslinking component is straightforward and easily accomplished by a protein chemist. See, for example, the techniques described in Li and Yamashiro, J. Amer. Chem. Soc., 92, 7608–7609 (1970) which is herein incorporated by reference. The resulting polypeptides have the structure X-[(elastomeric component)$_n$(crosslinking component)$_m$]$_l$-Y where X and Y represent any chemically compatible end group on the amino and carboxyl ends of the molecule, respectively, n is an integer from 5 to 100, m is an integer from 1 to 20, and l is an integer from 5 to 30. Block polymers are preferred, although random copolymers are also suitable. Block copolymers can be synthesized sequentially in an automatic peptide synthesizer or by reacting preformed units consisting of activated elastomeric and crosslinking units. If the latter method is used, it is preferred to use a shear stirring technique to orient the linear elastomeric units and to use EDCI as an activator. Relatively long reaction times and replenishment of EDCI during the course of reaction are preferred. Particularly preferred are polypeptides having molecular weights greater than 10,000 daltons. It is possible that one or more amino acid residue or segment of amino acid residues (such as the chemotactic segments later discussed) may be interspersed within the polypeptide chain so long as the elasticity and crosslinking ability of the resulting moelcule is not completely disrupted.

Examples of particularly preferred embodiments of the invention include the following, in which E represents an elastomic repeating unit (i.e., an elastomeric pentapeptide or tetrapeptide), H represents a chemotactic hexapeptide (later described), $XL_1$ represents the crosslinking component Ala-Ala-Ala-Ala-Lys-Ala-Ala-Lys-Tyr-Gly-Ala, $XL_2$ represents the crosslinking component Ala-Ala-Lys-Ala-Ala-Ala-Lys-Ala-Ala, n is an integer from 5 to 100, m is an integer from 1 to 20, and l is an integer from 5 to 30:

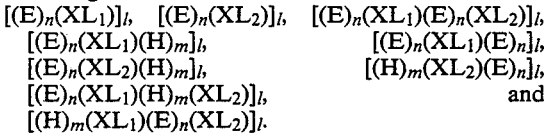

Examples of terminal X and Y end groups include the repeating peptide units themselves with free amino or carboxylic acid groups or salts thereof and peptide or amino acid units that have retained a blocking group that was present during synthesis of the polypeptide or that have a blocking group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the β-turn conformation of the elastomeric component or the crosslinking ability of the crosslinking component and does not confer bioincompatibility to the molecule as a whole.

In addition to the elastomeric and crosslinking components described above, the elastomeric copolymer of the invention may optionally comprise a chemotactic component selected from the group consisting of -Ala-Pro-Gly-Val-Gly-Val-, -Pro-Gly-Val-Gly-Val-Ala-, -Gly-Val-Gly-Val-Ala-Pro-, -Val-Gly-Val-Ala-Pro-Gly-, -Gly-Val-Ala-Pro-Gly-Val-, and -Val-Ala-Pro-Gly-Val-Gly-. These chemotactic components are described in copending application Ser. No. 533,670, filed on even date with the present application, which is herein incorporated by reference. Although small amounts of other amino acids or peptide fragments may be present in the elastomeric copolymers of the present invention, these copolymers are essentially devoid of peptide fragments which occur in natural elastin other than the elastomeric, crosslinking, and chemotactic components described above.

The relative amounts of the elastomeric and crosslinking components is relatively unlimited as long as elastomeric and crosslinking properties are retained by the copolymer product. However, it is preferred that the ratio of elastomeric component to crosslinking component be from 5 to 100 elastomeric repeating units per crosslinking component, with 10 to 20 being particularly preferred.

One limitation of the elastomic copolymer even when cross-linked, is that, while elastomeric, this material is somewhat lacking in strength, although the strength is sufficient for many purposes. The limited strength of the synthetic matrices is not unlike the biological situation, as the role of the elastic fibers is not one of load bearing but rather of providing resistance to extension, and of reforming the original tissue configuration when tension is released. Thus an improved prosthetic material can be produced by using a collagen-like load bearing component in addition to an elastomeric component of the correct elastic modulus. This can be achieved by compounding the synthetic elastomeric high polymers described above to a second material with greater strength. The second material forms the core of the composite fiber and will be referred to as the "collagen analogue" or "core fiber". The term core fiber is not limited to those forms of elastomeric composite materials in which a first fiber is coated with a second material, but also refers to other forms in which a strength giving fiber (the core fiber) is chemically bonded to a second component that is elastomeric (the polypeptide). For example, elastomeric polypeptide fibers may form strands between the segments of a crimped core fiber. The essential feature is that a chemical bond (of any type) exists between the surface of the core fiber and the elastomeric polypeptide so that the two components do not become separated while the elastomeric component is being stretched or is reforming the relaxed $\beta$-spiral. The chemical bond may be covalent or ionic bonding, hydrogen bonding, or the result of electrostatic interactions of various types, such as ion-dipole and diopole-dipole interactions. Covalent bonding is preferred. Linkages may be formed in any conventional manner and, if covalent bonds are to be formed, they can be accomplished by reacting a functional group of the polypeptide with a functional group of the core fiber. The functional groups may be present naturally as part of the polypeptide or core fiber or may be formed later, for example, by suitable chemical reactions involving the already formed core fiber or polypeptide. Such chemical reactions are well known and are discussed in more detail later in connection with cross-linking of the polypeptide.

The collagen analogue may be any fiber-forming natural or artificial material having a tensile strength of 10 to 50 kg/mm$^2$, preferably about 20 to 40 kg/mm$^2$, and most preferably about 30 kg/mm$^2$ and an elastic modulus of no more than $5 \times 10^{10}$ dynes/cm$^2$, that is biologically compatible with use in a living organism. By biologically compatible is meant that the core polymer, when compounded into the final product with the elastomer, will not harm the organism in which it is implanted to such a degree that implantation is as harmful as or more harmful than the needed vascular or other type of replacement. The term artifical fiber as used herein refers both to fibers formed from synthetic materials and to fibers formed from naturally occuring materials. The term artificial refers to the act of forming the fiber rather than the act of forming the material out of which the fiber is made. If used outside the living body of an organism is anticipated, biological compatibility is not required. Examples of suitable types of polymers which can form fibers of the required properties include polyamides, polyesters, polyvinyls, polyethylenes, polyurethanes, polyethers, and polyimides. Natural fibers include collagen, which is perferred. Non-polymeric fibers, such as metal fibers, and inorganic fibers, such as glass and carbon, may be of use in some applications, although their use is less preferred.

Suitable polyamides include polyamino acids, such as poly condensation products of p-aminobenzoic acid, and condensation products of diamines with dicarboxylic acids, such as hexamethylenediamine and terephthalic acids. Another suitable polyamide would be direct synthesis of an artificial fiber modeled after natural collagen. Polyesters suitable for use with the invention include poly(hydroxy acids) and condensation products of diols or polyols with dicarboxylic acids, such as ethylene glycol and an aromatic dicarboxylic acid. Examples of polyvinyls include poly(methyl methacrylate) and other esters of acrylic and methacrylic acid, polyvinyl alcohol, and esters of polyvinyl alcohol. Polyethylenes include polyethylene itself and halogenated derivatives of polyethylenes, such as polyvinyl chloride, as well as perhalogenated polyethylene, such as polytetrafluoroethylene. Polyurethanes include addition products of aromatic, aliphatic, or araliphatic diisocyanates with either diamines or diols. Polyethers include epoxy resins such as poly(propylenoxide) and poly(ethylene oxide). Polyimides include polymers derived from pyromellitic dianhydride and aromatic or aliphatic diamines.

Preferred collagen analogues are polyesters. Preferred polyesters are condensations products of phthalic, isophthalic, or terephthalic acid and diols, of which the most preferred are polymers derived from terephthalic acid and a 1,2-diol, such as, for example, the condensation product of terephthalic acid and ethylene glycol that is sold under the trademark of Dacron by E. I. duPont deNemours and Co. Polyesters having aromatic nuclei, such as Dacron, can be easily derivatized in order to provide function groups for covalent attachment of the polypeptide. For example, formylation and carboxylation of aromatic rings are easily carried out, well known reactions and provide functional groups that will react with amino groups present in the polypeptide.

The polymers listed above or other suitable materials are synthesized according to standard techniques and formed into fibers or fabrics, or are obtained from commercial sources as fibers or fabrics or in a form that may be manufactured into fibers or fabrics. Methods of preparing such fibers are well known and are not considered to be part of the present invention. The list given above is not intended to be limiting and any fiber or fabric that meets the standards of strength and biocompatability previously given may be used, whether known at the time of this application or discovered later. A crimping of the core fiber that will provide a uniform extendability of 200% or more is desirable. If the fiber is formed into a fabric, this crimping may be accomplished by the fabric weaving process. Crimping and expandable weaves are well known and are not considered to be part of the essence of the invention.

The diameter of the core fiber is not limited and may be varied as needed for the intended application. When the fiber is to be used in the formation of a vascular prosthesis, a diameter of less than 20 μm will give satisfactory results. Fibers with finer diameters will have a greater surface area per unit weight and are therefore preferred in order to allow better attachment of the elastomeric material to the surface of the collagen analogue (core fiber) and a more effective refolding of the collagen analogue. Diameters of less than 2 μm are preferred with a diameter of about 1 μm being most preferred.

If the elastomeric copolymer is to be compounded into a composite fiber, the weight ratio of the core fiber to the sheath component can vary as required for the intended use, with a ratio of from 10:1 to 1:10 being preferred, with from 1:1 to 3:10 being most preferred, when the composite fiber is to be used in a prothesis for a major artery. Lesser amounts of the elastomeric component, preferably about a 1:1 ratio, is preferred for a small artery prosthesis.

The two components of a composite fiber are brought together in any manner that results in the formation of a synthetic composite fiber in which the high strength polymeric fiber forms a core which is surrounded by a sheath of the polypeptide. It is desirable to have the elastomeric component bridge between folds in the collagen analogue. In general, this can be accomplished by coating a pre-formed, crimped polymeric fiber or woven fabric with a solution, suspension, or coacervate of the polypeptide, although it may be possible to spin or otherwise form the core fiber in a solution or suspension of the polypeptide.

A preferred method of forming the composite takes advantage of the property of coacervation exhibited by the elastomeric copolymer. The elastomer is generally soluble in water at temperaures below 20° C. but on raising the temperature above 20° C. the polymers associate and settle to form a dense, sticky phase called the coacervate. The process is entirely reversible, though dissolution can be slow. In order to impregnate the collagen analogue in preparation for compounding, fibers or strips of fabric made from the collagen analogue can be placed on the bottom of a chamber of like dimension. It is preferred to use a polytetrafluoroethylene chamber since the coacervates do not adhere well to polytetrafluoroethylene. Aqueous solutions containing the elastomeric copolymer are added to each chamber covering the fabric. The temperature is raised and the coacervate allowed to settle onto the surface of the fiber or into the weave of the fabric. If a fabric is used, it is preferred to largely fill the spaces between the fibers of the fabric. The supernatant can be either removed or allowed to dry down to the level of the fabric strip. The copolymer-impregnated strip or fibers are then removed from the chambers.

Other examples of methods of depositing the polypeptide on the surface of the core fiber include evaporation of solutions of the polypeptide on the surface of the fiber and reacting the polypeptide with functional groups present in the core fiber while the core fiber is suspended in a solution of the polypeptide.

It is generally desirable to cross-link the molecules of the polypeptide prior to use in vivo in order to increase its strength and elasticity. If a composite fiber is being formed, it is preferred to perform the cross-linking after the polypeptide has adhered to the core fiber. The method of creating the linkage is not limited to the methods disclosed in this application and may be any method of covalent or noncovalent linkage that does not prevent the elastomeric copolymer or the composite fiber from behaving as an elastomer. Suitable methods and types of linkages include cross-linking with ionizing irradiation and chemical modification or substitution of amino acid residues of the peptide repeating units and of the collagen analogue repeating units in order to form reactive side groups that undergo chemical reaction with each other (chemical cross-linking) e.g., by amide linkage, aldol condensation, Schiff base formation, enzymatic cross-linking by lysyl oxidase, or ester formation. Another suitable method of cross-linking comprises the use of photoactivated agents such as those giving rise to carbenes or nitrenes which may be attached as amino acid side groups or introduced as separate diffusible molecules.

A preferred type of chemical cross-linking occurs when polypeptides are prepared in which some of the repeating units are replaced by units in which one of the amino acid residues is replaced by the residue of an amino acid that has a reactive side chain. Preferred is preparation of a first batch of polypeptide in which a residue of some of the repeating units is replaced by an amino dicarboxylic acid, such as aspartic or glutamic acid, and a second batch of polypeptide in which a residue of some of the repeating units is replaced by a diamino carboxylic acid, such as lysine or ornithine. After a mixture of these two batches has been formed into a sheath around the core fiber, the free amino and carboxylic acid side group are allowed to react to create the cross-linkages. Formation of cross-linked PPP produced in this manner is described in U.S. Pat. No. 4,187,852, which is herein incorporated by reference. If chemical cross-linking is used, it is also necessary to provide reactive functional groups in the core fiber so that linkages between the peptide elastomer and the core fiber will also occur. Such modifications are well understood by polymer chemists and may include, for example, glycidyl esters of acrylates or methacrylates (as examples of reactive groups present during formation of the core polymer), or amino or carboxylic acid groups added to the terephthalic acid moeity of Dacron (as examples of reactive groups formed after formation of the core fiber).

The degree of cross-linking is such that elastomeric properties are imparted to the resulting composite fiber and can be varied to provide the desired dynamic mechanical properties. Preferred is an average of one cross-link for every 5 to 100 elastomer repeating units with 10 to 50 being most preferred. The degree of chemical cross-linking can be controlled by selecting the proper proportions of reagents. In general, the ratio of repeating units with reactive side groups to unmodified repeating units within a single molecule can vary from 1:1 to 1:20 with a ratio of about 1:5 being preferred. When two batches of polypeptide containing carboxylate or amino side groups as described above are used, the ratio of carboxylate-side-group-containing polypeptide to amino-side-group-containing polypeptide can vary from 4:1 to 1:4 with a ratio of about 1:1 being preferred.

When irradiation cross-linking is performed, a satisfactory approach is irradiation with gamma radiation from a cobalt-60 source. Other radiation energies required to provide a cross-linking action without excessive destruction of the core fiber or elastomeric peptide structure may be easily determined by simple experimentation. The degree of cross-linking is determined by the length of time and energy of the irradiation when irradiation cross-linking is performed. At least two cross-linkages per molecule are needed. The number of cross-linkages per molecule and the elastic modulus increase as the radiation dose increases. The requisite time for any desired amount of cross-linking is easily determined by simple experimentation for any given source of irradiation energy. Samples of non-cross-linked polymer or composite fiber are exposed to the source of ionizing energy for varying lengths of time, and the resulting elastic modulus is measured. In this manner the irradiation time required to produce an elastic modulus necessary to match a specific design characteristic of the polymer or composite fiber can easily be determined. For use in forming vascular wall prosthetic devices, an elastic (Young's) modulus of $10^6$ to $10^7$ dynes/cm$^2$, preferably about $4 \times 10^6$ dynes/cm$^2$, for the cross-linked composite fiber is desired. This is approximately the elastic modulus of the vascular wall.

Because the elastomeric copolymer of the invention is designed specifically to act as an in vivo substrate for lysyl oxidase, it is also possible to use lysyl oxidase in vitro in order to produce the necessary strength-giving crosslinks during the manufacturing of the shaped final component. Crosslinking is easily accomplished by contacting peptide chains of the invention with a solution containing lysyl oxidase, preferably in an amount of from $10^3$ to $10^6$ units per milligram of peptide.

The elastomeric copolymers of the invention may comprise both single strands and crosslinked chains prepared from single strands. In all cases, an essential feature of the invention is the availability of free cross-linking units for interaction with the regenerating tissue in vivo. Accordingly, if cross-linking components are present in single strands and these components are used during the formation of the strength-giving crosslinks in the manufacturing process, it is necessary that at least one free cross-linking component be present per elastomeric copolymer, on the average, although from 1 to 20 free cross-linking units per 1000 amino acid residues of the entire polypeptide elastic copolymer is preferred.

The elastomeric composite fibers may be woven into a fabric or an elastomeric fabric may be formed from a fabric of the core fiber material by coating and cross-linking the polypeptide on the surface of the fibers of the preformed fabric. When the resulting fabric has an elastic modulus of from $10^6$ to $10^7$ dynes/cm$^2$ and has been formed into an appropriate shape, for example, a tubular shape, the resulting article may be used in vascular prosthesis. One simple way to obtain the desired tubular form, not considered to be limiting, would be to place the preformed woven and crimped tube of core fiber material between two concentric tubes (e.g., glass tubes) with the outer tube containing an aqueous solution of the elastomeric copolymer. The temperature of the solution would then be raised to allow coacervation to take place and the resulting impregnated woven fabric composition would be cross-linked by γ-irradiation at an appropriate dose.

It is also possible to form separate strength-giving and elastomeric fibers and to interweave them into a fabric of the desired shape. The first fiber, which is essentially non-elastic, would provide strength while the elastomeric polypeptide fiber would provide elasticity.

Once the synthetic composite material has been formed into an appropriate shape, if it is intended for use as a vascular replacement or patch, it is surgically inserted into a human or animal in place of diseased or missing vascular material. Tubular material may be used to replace an entire vein or artery by attaching each end to the distal and proximal free ends of a blood vessel having a missing or surgically removed section. Attachment is made so that blood flows through the tube without major leaking by any means capable of providing medically acceptable attachment, such as suturing or cauterizing. The elastomeric composite may be made in the form of a patch to be attached by the same methods if replacement of only a portion of a blood vessel is desired. Also tubular material may be used as a lining to replace diseased tunica intima following endarterectomy.

Other uses of the elastomic material of this invention are also contemplated. The elastomer itself or the composite elastomeric fiber can be formed into sutures or used in the formation of artificial ligaments. As was previously described, the elastic modulus is easily controlled, resulting in a material having broad use, both in biological systems for replacement and repair of natural parts of an organism and in the myriad of nonbiological uses presently fulfilled by other elastomers. Thus any natural elastic system, especially those in which tropoelastin or elastin is naturally present, can be repaired by replacing a damaged portion of the system, such as a ligament, tendon, blood vessel wall, or the like, with an artificial elastomeric copolymer of the invention.

The above disclosure generally describes the present invention. A more complete understanding can be obtained by reference to the following specific examples of polypeptide chains, which are provided herein for purposes of illustration only and are not intended to be limiting unless otherwise specified. In these examples, A represents an alanine residue, G represents a glycine residue, Y represents a valine residue, L represents a lysine residue, T represents a tyrosine residue, P represents a proline residue, and D represents a D-valine residue I. a random copolymer of VPDVG and AALAA in a 20:1 molar ratio, average molecular weight of 15,000.

II. a block copolymer comprising (1) a random copolymer of VPGG and VPGVG in a 1:4 ratio having an average molecular weight of 8000 and (2) AAAA-LAATGA, average molecular weight of 120,000 for the block copolymer.

III. a block copolymer of $[(VPGVG)_{15}(AALAAALAA)(APGVGV)_5]_n$, average molecular weight of 200,000.

IV. a random copolymer of VPGVG, VPGG, and AAAALAATGA in a 15:5:1 molar ratio, average molecular weight 80,000.

V. a composite fiber consisting of the elastomeric copolymer of Example III crosslinked by irradiation on the surface of a 1 -μm diameter, crimped Dacron core fiber in a weight ratio of 1:2 (elastomer: core fiber).

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A synthetic elastomeric copolymer, which comprises:

an elastomeric component selected, from the group consisting of tetrapeptide repeating units, pentapeptide repeating units and mixtures thereof wherein said repeating units comprise amino acid residues selected from the group consisting of hydrophobic amino acid and glycine residues and said repeating units exist in a conformation having a β-turn, and a crosslinking component selected from the group consisting of amino acid or peptide residues of the formula

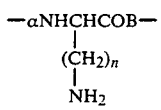

wherein α represents a covalent bond or a peptide fragment containing 1–10 α-helix-forming amino acid residues, B represents a covalent bond or a peptide fragment containing 1–10 amino acid residues, and n is an integer from 2 to 6.

2. The elastomeric copolymer of claim 1, wherein a crosslinking component has the formula

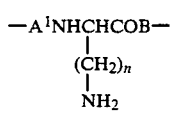

wherein $A^1$ represents a peptide fragment consisting of 2–10 α-helix-forming amino acid residues.

3. The elastomeric copolymer of claim 2, wherein B is $A^2B^1$ wherein $A^2$ represents a peptide fragment consisting of 2 or 3 α-helix-forming amino acid residues and $B^1$ represents

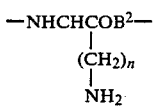

wherein $B^2$ represents a covalent bond or a peptide fragment consisting of 1–6 amino acid residues.

4. The elastomeric copolymer of claim 3, wherein $B^2$ represents 2–4 amino acid residues.

5. The elastomeric copolymer of claim 3, wherein $B^2$ represents -Tyr-Gly-Ala-or -Ala-Ala-.

6. The elastomeric copolymer of claim 1, wherein said α-helix-forming amino acid residues are alanine, leucine, methionine, glutamine, tryptophan, valine, phenylalanine, or isoleucine residues.

7. The elastomeric copolymer of claim 1, wherein said α-helix-forming residues are alanine or leucine residues.

8. The elastomeric copolymer of claim 1, wherein said α-helix-forming residues are alanine residues.

9. The elastomeric copolymer of claim 1, wherein n is 4.

10. The elastomeric copolymer of claim 3, wherein said α-helix forming amino acid residues are alanine, leucine, methionine, glutamine, tryptophan, valine, phenylalanine, or isoleucine residues.

11. The elastomeric copolymer of claim 10, wherein n is 4.

12. The elastomeric copolymer of claim 11, wherein said crosslinking component comprises the formula

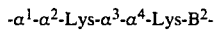

or $-\alpha^1-\alpha^2$-Lys-$\alpha^3$-$\alpha^4$-$\alpha^5$-Lys-$B^2$- wherein $\alpha^1$-$\alpha^5$ independently represent α-helix-forming amino acid residues.

13. The elastomeric copolymer of claim 12, wherein $\alpha^1$-$\alpha^5$ each represents alanine.

14. The elastomeric copolymer of claim 13, wherein $B^2$ represents -Tyr-Gly-Ala- or Ala-Ala.

15. The elastomeric copolymer of claim 1, wherein said hydrophobic amino acid residues are selected from the group consisting of hydrophobic α-amino acids.

16. The elastomeric copolymer of claim 15, wherein said hydrophobic amino acid residues are selected from the group consisting of alanine, valine, leucine, isoleucine, proline, phenylalanine, tryptophan, and methionine.

17. The elastomeric copolymer of claim 16, wherein the first amino acid residue of said repeating unit is a residue of valine, leucine, or isoleucine.

18. The elastomeric copolymer of claim 16, wherein the second amino acid residue of said repeating unit is a residue of proline.

19. The elastomeric copolymer of claim 16, wherein the third amino acid residue of said repeating unit is a residue of glycine or a hydrophobic amino acid of opposite chirality having no more than 10 carbon atoms in the side chain of said residue.

20. The elastomeric copolymer of claim 16, wherein the fourth amino acid residue of said repeating unit is a residue of valine.

21. The elastomeric copolymer of claim 16, wherein the fifth amino acid residue of said repeating unit is a residue of glycine.

22. The elastomeric copolymer of claim 1, wherein said repeating unit is L-Val-L-Pro-D-Ala-L-Val-Gly, L-Val-L-Pro-Gly-L-Val-Gly, or L-Val-L-Pro-Gly-Gly, or L-Val-L-Pro-D-Ala-Gly.

23. The elastomeric copolymer of claim 1, wherein the molecules of said elastomeric polypeptide are crosslinked by covalent bonding.

24. The elastomeric material of claim 23, wherein said molecules are crosslinked by irradiating said polypeptide with ionizing radiation.

25. The elastomeric material of claim 23, wherein said molecules are crosslinked by reacting a first chemically reactive side group of a modified amino acid residue of a first molecule of said polypeptide with a second chemically reactive side group of a modified amino acid residue of a second molecule of said polypeptide.

26. An elastomeric composite material, comprising:
an artifical core fiber, and
the elastomeric material of claim 1 chemically bonded to the surface of said core fiber.

27. The elastomeric material of claim 26, wherein the weight ratio of said core fiber to said polypeptide is from 10:1 to 1:10.

28. An elastomeric composite material comprising an essentially non-elastic first artificial fiber, and a second fiber chemically attached to the surface of said first fiber, wherein said second fiber comprises the elastomeric material of claim 1.

29. A blood vessel prosthesis comprising the material of claim 1 in the form of a patch or hollow tube.

30. The elastomeric copolymer of claim 1, wherein said copolymer further comprises a chemotactic component selected from the group consisting of -Ala-Pro-Gly-Val-Gly-Val-, -Pro-Gly-Val-Gly-Val-Ala-, -Gly-Val-Gly-Val-Ala-Pro-, -Val-Gly-Val-Ala-Pro-Gly-, -Gly-Val-Ala-Pro-Gly-Val-, and -Val-Ala-Pro-Gly-Val-Gly-.

* * * * *